United States Patent [19]

Barreras et al.

[11] Patent Number: 4,558,702
[45] Date of Patent: Dec. 17, 1985

[54] CARDIAC PACER HAVING INPUT/OUTPUT CIRCUIT PROGRAMMABLE FOR USE WITH UNIPOLAR AND BIPOLAR PACER LEADS

[75] Inventors: Francisco J. Barreras, Miami, Fla.; James P. Martucci, Palatine, Ill.

[73] Assignee: Cordis Corporation, Miami, Fla.

[21] Appl. No.: 459,806

[22] Filed: Jan. 21, 1983

[51] Int. Cl.[4] .............................................. A61N 1/36
[52] U.S. Cl. .............................. 128/419 PG; 128/902
[58] Field of Search ................................. 128/419 PG

[56] References Cited

U.S. PATENT DOCUMENTS 4,055,189 10/1977 Auerbach et al. ............ 128/419 PG
4,402,322 9/1983 Duggan .......................... 128/419 PG

FOREIGN PATENT DOCUMENTS 0030897 12/1980 European Pat. Off. ...... 128/419 PG
2026870 2/1980 United Kingdom ......... 128/419 PG Primary Examiner—William E. Kamm
Attorney, Agent, or Firm—Lockwood, Alex, Fitzgibbon & Cummings

[57] ABSTRACT

An implantable cardiac pacer having atrial and ventricular electrodes includes an input/output circuit which can be programmed for use with either unipolar or bipolar pacer leads. The circuit can be reprogrammed by the physician after implant to accommodate physiological changes in the patient or chronic changes in pacer lead characteristics, and can be utilized with single channel or dual channel cardiac pacers.

7 Claims, 7 Drawing Figures

CARDIAC PACER HAVING INPUT/OUTPUT CIRCUIT PROGRAMMABLE FOR USE WITH UNIPOLAR AND BIPOLAR PACER LEADS

BACKGROUND OF THE INVENTION

The present invention is directed generally to cardiac pacers, and more particularly to an input/output circuit for a cardiac pacer programmable for use with either bipolar or unipolar leads.

Implantable battery operated cardiac pacers require one or more pacer leads for establishing electrical connection between their input/output terminals, and the atrium and/or the ventricle of the heart. Such leads, which are typically of the endocardial type for direct implantation in the heart, may be of either unipolar (UNIP) construction, wherein the implanted lead provides a cathode electrode and an anode electrode is provided through the pacer housing or other suitable means, or of bipolar (BIP) construction, wherein the implanted lead provides both the cathode and anode electrodes, and the pacer housing is isolated from the electrical circuit.

Depending on the particular application, the use of one or the other of the two lead types may be advantageous. Unipolar leads have the advantage of being physically smaller, and of providing less energy loss and greater sensitivity than bipolar leads. Bipolar leads have the advantage of providing improved noise rejection, improved immunity against undesired muscle stimulation, and reduced susceptibility to artifacts resulting from patient movement.

The choice of lead type is made by the physician at the time of implant, depending on the particular pacing requirements of the patient and any problems encountered with either the sensing or pacing functions. Once implanted, the pacer and leads are inaccessible except by invasive surgical procedures. In the past in those instances where a change in lead configuration has been necessary (i.e. BIP to UNIP, or UNIP to BIP), it has been necessary to surgically remove the pacer for reconfiguration, thereby subjecting the patient to the risk of complications.

The problem of post-implant lead reconfiguration is more prevalent with pacers having two electrodes; one for sensing and/or pacing the atrium, and one for sensing and/or pacing the ventricle. These pacers are typically utilized in treating more complex cardiac dysfunctions and are susceptible to cross-talk between atrial and ventricular leads, as well as to the previously outlined sensitivity and isolation problems. While many of such two electrode pacers incorporate a multiplex circuit which enables the pacer to be non-invasively reprogrammed by means of external control apparatus, there has heretofore been no provision for reconfiguring the pacer input/output circuitry for alternate lead arrangements.

The present invention provides an input/output circuit for a cardiac pacer which enables the use of either UNIP or BIP lead configurations, for either sensing or pacing, as programmed by the physician, eithout the necessity of making physical changes to the pacer or its leads.

Accordingly, it is a general object of the present invention to provide a new and improved cardiac pacer.

It is a more specific object of the invention to provide a new and improved cardiac pacer having an input/output circuit programmable for use with either UNIP or BIP pacer leads.

It is a more specific object of the invention to provide an input/output circuit for a dual channel cardiac pacer which offers improved sensitivity and inter-channel isolation.

SUMMARY OF THE INVENTION

The invention is directed to an input/output circuit for a cardiac pacer which is selectively operable in unipolar and bipolar pacing and sensing modes in response to an applied command signal. The circuit includes at least one pacer lead terminal having cathode and anode electrodes, a differential amplifier having inverting and non-inverting inputs, coupling means for coupling respective ones of the electrodes to the inputs, and reference electrode means for establishing contact with a resident body. First, second and third switching means responsive to first, second and third applied mode control signals developed by a mode control circuit responsive to the command signal selectively connect the electrodes to a plane of reference potential to establish bipolar or unipolar sensing and pacing.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
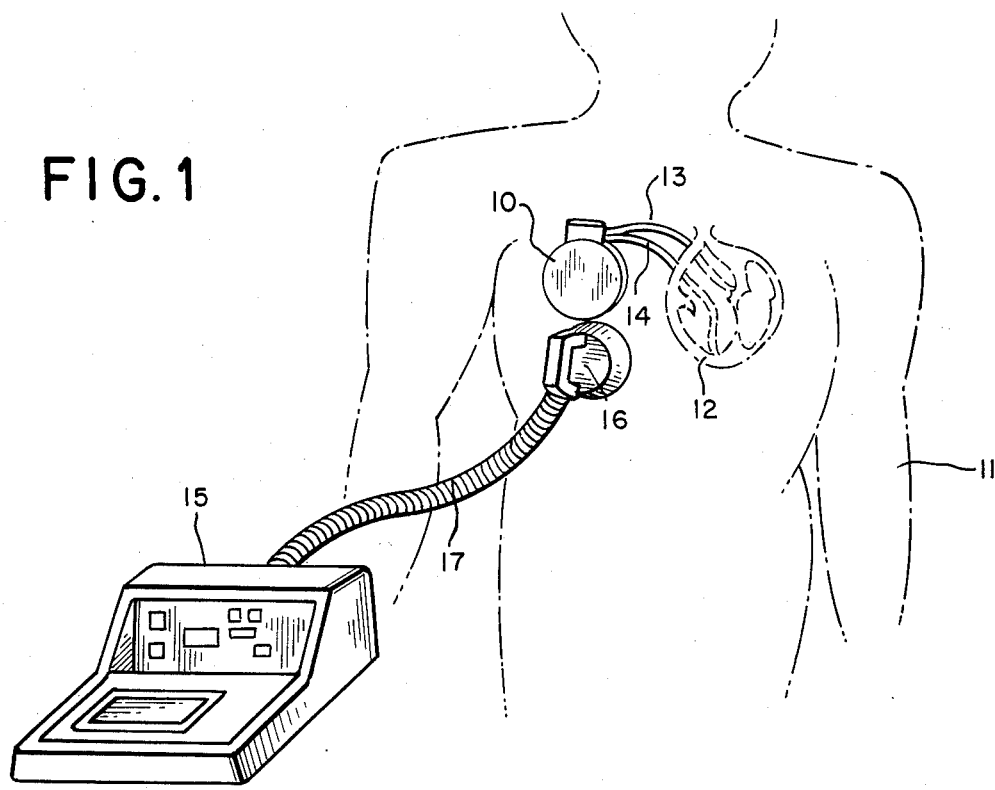
FIG. 1 is a perspective view of a battery powered implantable cardiac pacer including a universal externally programmable input/output circuit constructed in accordance with the invention.

Referring to the Figures, and particularly to FIG. 1, a battery-operated implantable programmable cardiac pacer 10 is shown implanted within a patient 11. The output of the pacer is connected to the patient's heart 12 (shown in cross section) by means of pacer leads 13 and 14, which may be conventional in construction and operation. The pacer 10 is preferably formed as a self-contained and hermetically sealed device such that its operation is unaffected by exposure to body fluids.

Operation of the pacer can be modified as required by specific application by means of a multiplex-type monitor and control programmer apparatus 15 external to the patient. The apparatus, which may be conventional in design and construction, includes a number of user-actuable controls by which the user can selectively vary certain operating functions and parameters of the pacer, including, in accordance with the invention, the input-/output lead configuration. Communication between the control apparatus 15 and the pacer is provided by a magnetic or radio-frequency transceiver 16 postioned by the user on the chest of the patient in close proximity to the implanted pacer. The transceiver transmits and receives telemetry data to and from the pacer in a manner well known to the art, and the resulting electrical signal is conveyed to and from the apparatus through a flexible electrical cable 17. In use, the input/output circuits of pacer 10 can be configured to operate in either a bipolar (BIP) mode or in a unipolar (UNIP) mode by actuating appropriate switches on apparatus 15.

Figure 2:
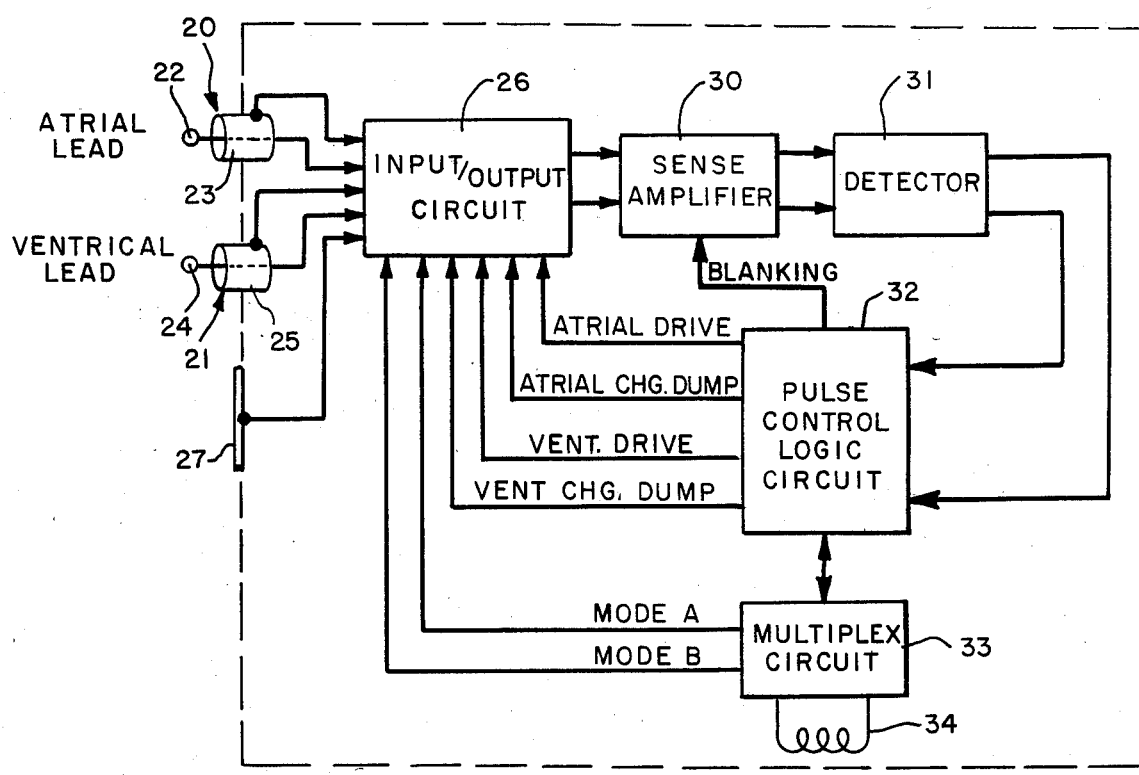
FIG. 2 is a functional block diagram showing the principal elements of the cardiac pacer of FIG. 1.

Referring to FIG. 2, the implanted cardiac pacer 10 is seen to include an atrial terminal 20 for connection to the atrium of the heart, and a ventricular terminal 21 for connection to the ventricle of the heart. These terminals are each coaxial in construction. The atrial terminal 20 includes a cathode electrode 22 and a sleeve-shaped anode electrode 23. Similarly, the ventricular terminal 21 includes a central cathode electrode 24, and a sleeve-shaped anode electrode 25. The cathode and anode electrodes of each terminal are connected to an input-/output circuit 26 wherein, in accordance with the invention, appropriate connections are established between the electrodes and the sensing and pacing circuitry of the pacer in accordance with a user-selected sense/pace operating mode. An additional electrode 27, which may comprise the electricallyconductive surface of the pacer housing, is also connected to input/output circuit 26.

R-wave and P-wave signals developed on the atrial and ventricular terminals are applied to a sense amplifier 30 for amplification. Preferably, sense amplifier 30 has a bandpass characteristic which attenuates noise and other extraneous signals picked up by the pacer leads, so that the detected waves can be more effectively amplified. The amplified sense signals are applied to a detector 31, which provides output pulses upon occurrence of the respective wave components in the sensed signal. The detector output pulses are applied to a pulse control logic circuit 32, which under appropriate circumstances produces atrial and ventricular drive pulses for application to the input/output circuit 26. These drive pulses cause generation of pacer output pulses of predetermined amplitude and duration on the atrial and ventricular terminals for application to respective chambers of the heart by pacer leads 13 and 14.

The control pulses applied to the input/output circuit 26 include in addition to the atrial and ventricular drive pulses, atrial and ventricular charge dump pulses, which provide for a rapid depolarization of the electrodes immediately following each generated pacer pulse. Also, atrial and ventricular blanking pulses deactivate the sense amplifiers for approximately the duration of the drive and charge dump pulses from either channel.

The operation of the pulse control logic circuit 32 may be controlled from an external location by means of multiplex circuit 33, which is adapted to receive on a pick-up element 34 an appropriately coded radio-frequency or magnetic control signal and generate appropriate control signals for application to pulse control logic circuit 32. As provided by the invention, multiplex circuit 33 also provides two binary mode control signals, designated mode A and mode B signals, which are applied to input/output circuit 26 to control the interconnect mode of the circuit. Depending on the logic state of the two mode signals, input/output circuit 26 is conditioned to one of the following four operating modes: UNIP sensing and UNIP pacing; or BIP sensing and BIP pacing; or UNIP sensing and BIP pacing; or BIP sensing and UNIP pacing.

Figure 3:
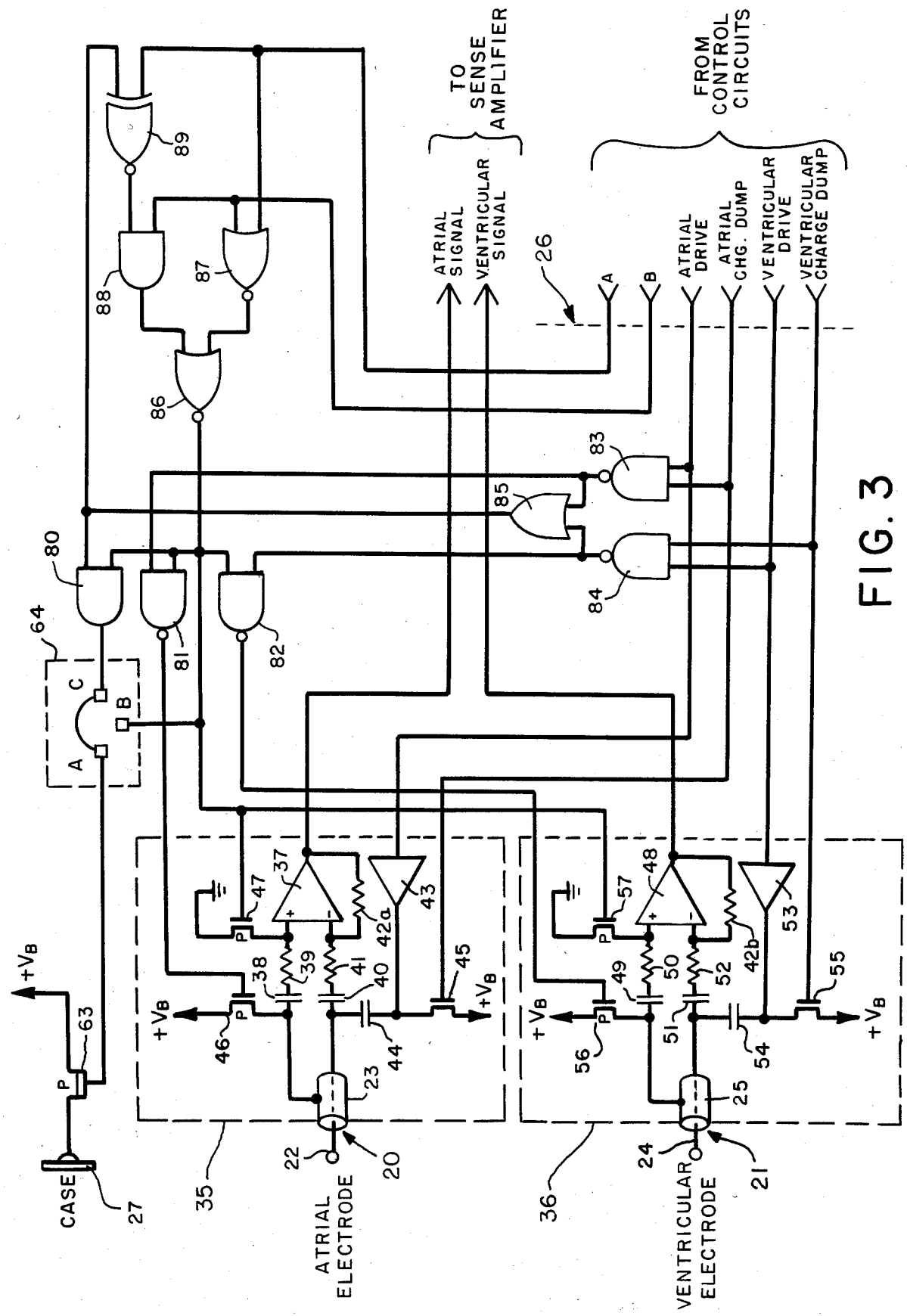
FIG. 3 is a simplified schematic diagram of the input/output circuit of the cardiac pacer.

Referring to FIG. 3, the input/output circuit 26 of the pacer is seen to include an atrial circuit 36 and a ventricular circuit 36 within which atrial and ventricular signals are sensed and respective pacing pulses are developed. For accomplishing the sensing functions the atrial input circuit includes a differential amplifier 37 for amplifying atrial signals received on terminal 20. The cathode 22 of terminal 20 is connected to the inverting input of the differential amplifier through a capacitor 38 and a resistor 39, and the anode 23 of terminal 20 is connected to the non-inverting input of the differential amplifier through a capacitor 40 and a resistor 41. A resistor 42 connected between the output and the inverting input of differential amplifier 37 provides degenerative feedback in accordance with conventional practice.

The atrial pacing function is accomplished by means of a pulse amplifier 43, which may be conventional in design and operation, and a capacitor 44 connected between the output of the amplifier and cathode electrode 22. In operation, amplifier 43 periodically produces output pulses in response to atrial drive signals developed in the pacer pulse control logic circuit 32.

To enable operation in both BIP and UNIP modes, and to provide a charge dump function following each atrial pacing pulse, the atrial circuit 35 includes in accordance with the invention PMOS transistors 45, 46 and 47. Transistor 45 includes principal electrodes connected between the output of amplifier 43 and the pacer battery $+V_B$, which forms the signal ground of the pacer. Transistor 46 includes principal electrodes connected between anode 20 and $+V_B$, and transistor 47 includes principal electrodes connected between the non-inverting input of amplifier 48 and system ground.

The ventricular circuit 36 includes a differential amplifier 48 for amplifying ventricular signals received on terminal 21. The cathode 24 of terminal 21 is connected to the inverting input of the differential amplifier through a capacitor 49 and a resistor 50, and the anode 25 of terminal 21 is connected to the non-inverting input of the differential amplifier through a capacitor 51 and a resistor 52. A resistor 42b connected between the output and the inverting input of differential amplifier 48 provides degenerative feedback in accordance with conventional practice.

The ventricular pacing function is accomplished by means of a pulse amplifier 53, which may be conventional in design and operation, and a capacitor 54 connected between the output of the amplifier and cathode electrode 24. In operation, amplifier 48 periodically produces output pulses in response to ventricular drive signals developed in the pacer pulse control logic circuit 32.

To enable operation in both BIP and UNIP modes, and to provide a charge dump function following each ventricular pacing pulse, the ventricular circuit 36 includes, in accordance with the invention, PMOS transistors 55, 56 and 57. Transistor 55 includes principal electrodes connected between the output of amplifier 53 and $+V_B$. Transistor 56 includes principal electrodes connected between anode 25 and $+V_B$, and transistor 57 includes principal electrodes connected between the non-inverting input of amplifier 48 and system ground.

Figure 4:
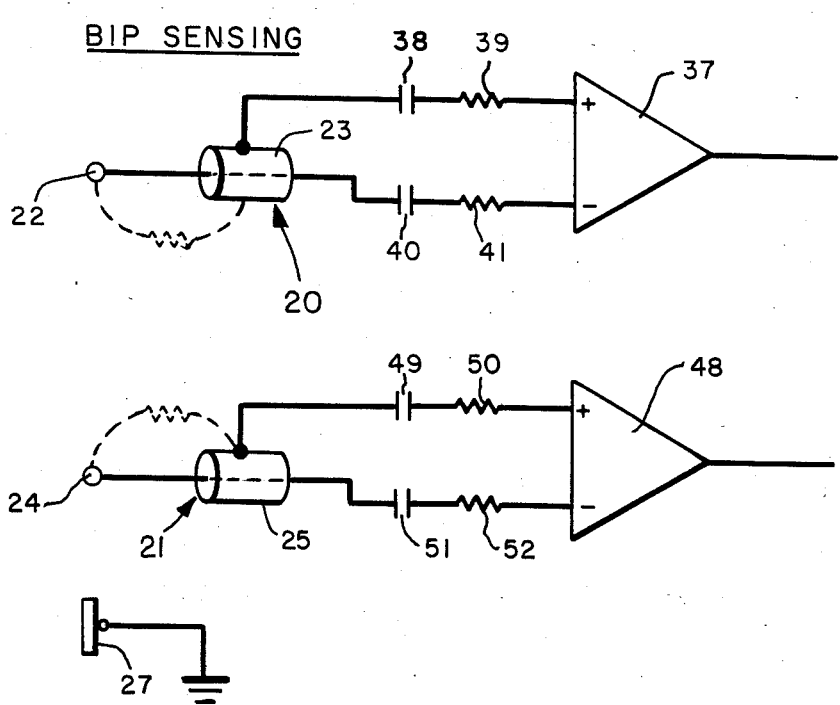
FIG. 4 is a simplified schematic diagram of the input/output circuit showing the principal components thereof configured for BIP sensing.

When the atria terminal is connected to a bipolar pacer lead and input circuit 35 is conditioned for bipolar (BIP) sensing by biasing transistors 45-57 to cut-off, as shown in FIG. 4, any signal developed between the pacer lead tip electrodes of the connected bipolar lead is impressed through capacitors 38 and 40 to differential amplifier 37, wherein it is amplified for application to the pacer atrial sensing circuit. However, because of the balanced input, the differential amplifier does not respond to common-mode signals, such as artifacts and other interference signals, which appear on both terminals simultaneously.

Figure 5:
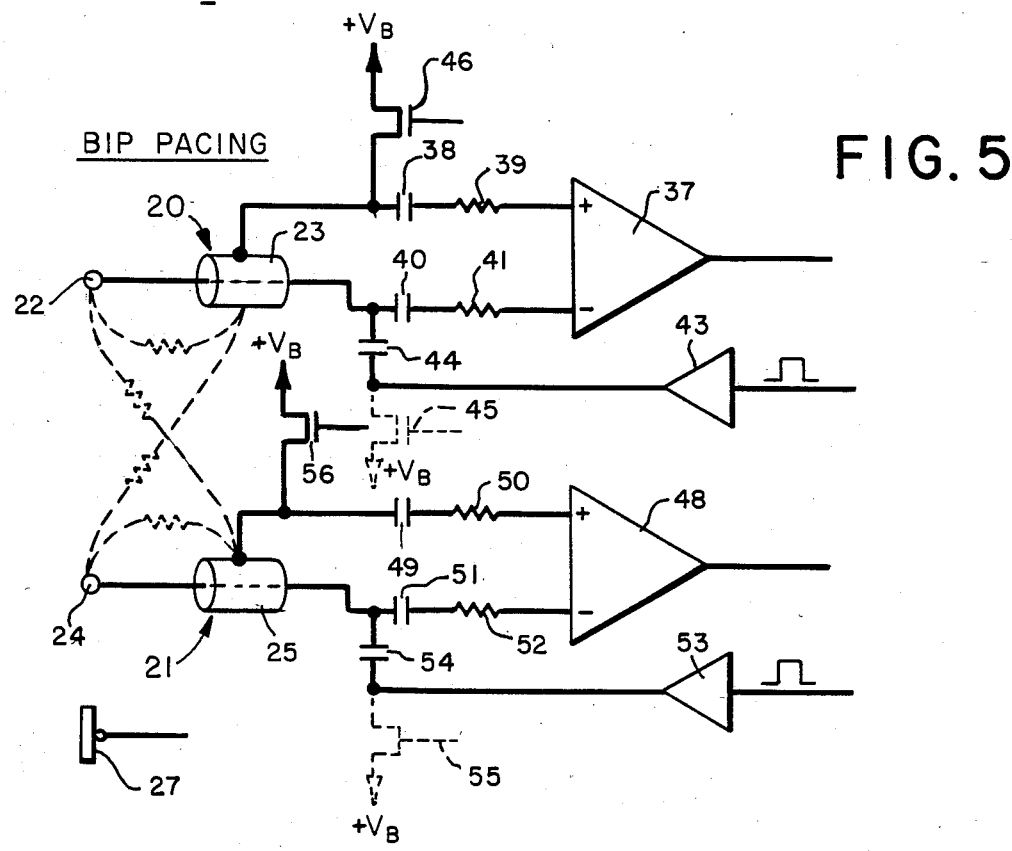
FIG. 5 is a simplified schematic diagram of the input/output circuit showing the principal components thereof configured for BIP pacing.

When pacing in the BIP mode, as shown in FIG. 5, transistor 46 is biased into saturation, effectively grounding anode electrode 23 relative to any applied signal. Atrial stimulation pulses developed by amplifier 43 in response to applied atrial drive signals are applied to cathode electrode 22 through capacitor 44. Since the anode electrode is at signal ground, and transistor 63 is cut-off, the result is that virtually the entire output signal appears across the tip electrodes of the connected bipolar atrial pacer lead.

The ventricular channel 36 is similarly configured for BIP/UNIP sensing and pacing. In the BIP sensing mode transistors 55-57 are biased into cut-off, as shown in FIG. 4, and ventricular signals present on the tip electrodes of a connected bipolar lead are applied to the inverting and non-inverting input terminals of differential amplifier 48. In the BIP pacing mode, as shown in FIG. 5, transistor 56 is biased into saturation, effectively grounding cathode electrode 25, and transistor 63 is biased into cut-off, causing substantially the entire output signal to appear across the tip electrodes of the connected bipolar ventricular pacer lead.

Figure 6:
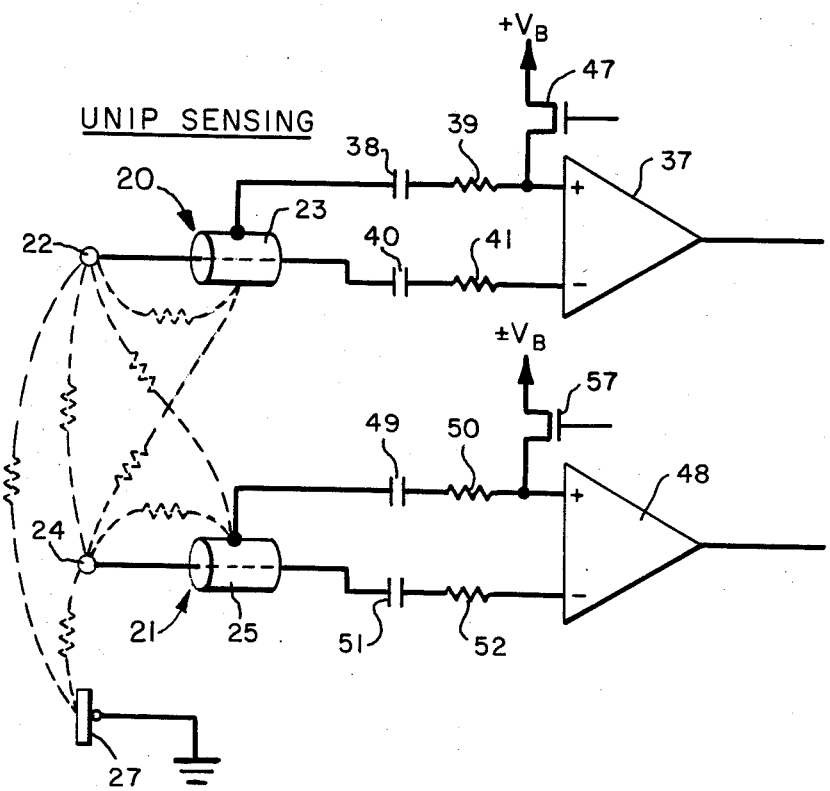
FIG. 6 is a simplified schematic diagram of the input/output circuit showing the principal components thereof configured for UNIP sensing.

When the input/output circuit 26 is conditioned for UNIP sensing, as shown in FIG. 6, within atrial channel 35 transistor 47 is biased into saturation, causing the non-inverting input of differential amplifier 37 to be effectively connected to signal ground. This results in the signal received on the tip electrode of the connected UNIP pacer lead to be applied to the inverting input. The case electrode 27 may be connected to $+V_B$ at this time by a PMOS transistor 63, depending on the strapping of terminals A, B and C of a terminal block 64 on the pacer housing, to provide a return path through body fluid for the sensed signal.

The operation of ventricular channel 36 in the UNIP sensing mode is similar to that of channel 35. Transistor 57 is biased into saturation, causing the non-inverting input of differential amplifier 48 to be effectively at signal ground, and the ventricular signal developed on the tip electrode of the connected unipolar lead to be applied to the inverting input of differential amplifier 48.

Figure 7:
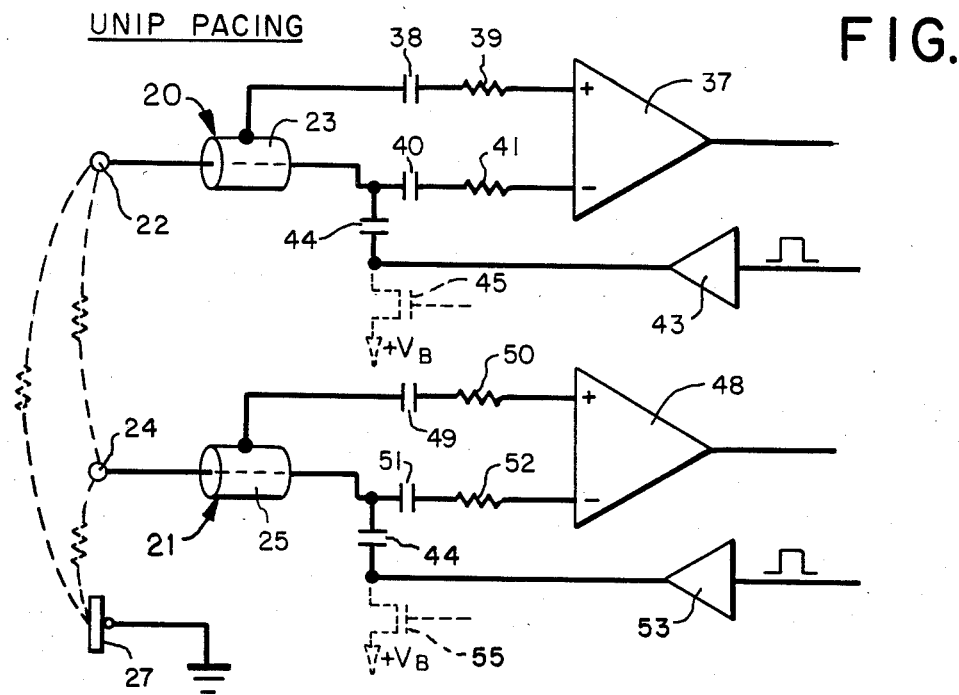
FIG. 7 is a simplified schematic diagram of the input/output circuit showing the principal components thereof configured for UNIP pacing.

When pacing in the UNIP mode, as shown in FIG. 7, transistors 45-47 in atrial channel 35 are biased into cut-off, causing the output pulse developed by amplifier 43 to be applied only to cathode electrode. To provide a return path for the pacer signal transistor 63 is biased into saturation by an applied control signal to connect the pacer housing to system ground. Thus, connected, the body fluids to which the pacer housing is exposed provide an electrical path to the heart.

Operation of the ventricular channel 36 in the UNIP pacing mode is similar to that of channel 35. Transistors 55-57 are biased to cut-off, and the output pulse developed by amplifier 53 is applied to cathode electrode 24. The grounded case electrode 27 provides a return path for the pacing pulse.

The conduction state of transistors 45 and 55 is controlled by respective atrial and ventricular charge dump signals developed in pulse control logic circuit 32 and applied to the control electrodes of the devices on lines 73 and 74. These signals cause respective ones of transistors 45 and 55 to be driven into saturation for a short period of time following each atrial and ventricular output pulse, thereby discharging respective ones of capacitors 44 and 54 and allowing rapid depolarization of the associated electrodes.

Atrial and ventricular drive pulses required for producing output pulses from amplifiers 43 and 48 are developed by pulse control logic circuit 32 and applied to the inputs of the amplifiers on lines 75 and 76, respectively. P-waves detected by the atrial pacer lead and amplified by differential amplifier 37 are applied to sense amplifier 30 (FIG. 2) by way of a signal line 77. R-wave signals detected by the ventricular pacer lead and amplified by differential amplifier 48 are applied to sense amplifier 30 by way of a signal line 78.

In accordance with the invention, the atrial and ventricular channels 35 and 36 may be conditioned to sense and/or pace in either a bipolar (BIP) or unipolar (UNIP) mode. To this end, the input/output circuit 26 includes a mode control circuit comprising an AND gate 80, a plurality of NAND gates 81-84, an OR gate 85, a pair of NOR gates 86 and 87, an AND gate 88, and an exclusive NOR gate 89. The purpose of these logic elements is to generate appropriate control signals to condition transistors 45, 47, 55, 57 and 63 into either cut-off or saturated states, as required by the operator-selected input/output mode.

As previously developed, the input/output operating mode is determined by A and B mode designation signals developed in multiplex circuit 33. These mode designation signals are applied on respective control lines 90 and 91 to inputs of various ones of the logic elements, as shown in FIG. 3, to obtain pacing and sensing modes in accordance with the following table:

| A | B | SENSE | PACE |
|---|---|-------|------|
| 0 | 0 | UNIP  | UNIP |
| 1 | 0 | BIP   | BIP  |
| 0 | 1 | UNIP  | BIP  |
| 1 | 1 | BIP   | UNIP |

In the bipolar pacing and sensing mode, during sensing the output of AND gate 70 is logic low, causing transistor 63 to conduct and connect the pacer housing electrode 27 to system ground ($+V_B$). At the same time, transistors 46 and 56 are rendered non-conductive by the logic low outputs of NAND gates 81 and 82, so that differential sensing may be accomplished through the bipolar electrodes 22 and 23 for atrial sensing, and the bipolar electrodes 24 and 25 for ventricular sensing.

During an output pulse and subsequent charge dump (discharge of the output capacitor), the output logic OR gate 85 becomes logic high, causing the output of logic AND gate 80 to become logic high. This biases transistor 63 into cut-off, and isolates the pacer housing electrode 27 from the system ground. At the same time, either NAND gate 81 or NAND gate 82 will provide a logic low output, depending on which output channel is active, to bias on the respective one of transistor 46 or transistor 56 for bipolar pacing. If contacts A and B of interconnect pad 64 are jumpered (instead of contacts A and C), then transistor 63 does not become conductive in the bipolar sensing mode, resulting in ungrounded differential sensing occurring.

In a unipolar pacing/bipolar differential sensing mode, the A mode control signal and the B mode control signal are both logic high. This causes transistors 46 and 56 to be cutoff during sensing, and transistor 63 to be in saturation if contacts A and C are connected. As a result, each chamber of the heart is sensed in a differential mode with the pacemaker's housing serving as a ground electrode. If contacts A and B are connected (instead of A and C), then transistor 63 will be cutoff during sensing and no ground electrodes will be available. During an output pulse and subsequent charge dump, the appropriate one of transistors 56 and 46 will remain cut off and transistor 63 will remain conductive.

In the unipolar pacing and sensing mode, both mode control signals A and B are logic low, causing transistor 63 to be conductive and transistors 46 and 56 to be cut-off at all times. Transistors 60 and 61 are also rendered conductive in this mode, so that the non-inverting inputs to the differential amplifiers are clamped to the reference voltage. Consequently, differential amplifiers 40 and 50 become single ended amplifiers, providing sensing between the pacer's case and the cathode's electrodes.

In the bipolar pacing and unipolar sensing mode, the mode A control signal is logic low and the mode B control signal is logic high. This causes transistors 46 and 56 to be cut off, and transistor 63 to become conductive during sensing. During pacing and subsequent charge dump the outputs of NAND gates 81 and 82 become logic high. Depending on which channel is active, either transistor 46 or transistor 56 will become conductive. Transistor 63 is cut off at this time to disconnect the unipolar anode from the system.

Thus, the operator is able to designate one of four operating modes as required by a particular situation. Each of these operating configurations provides certain advantageous features which may be particularly advantageous in certain situations, as outlined in the following table:

| SENSING | PACING | |
| --- | --- | --- |
| BIP | UNIP | Minimizes loss of energy at the output lead and prevents false inhibition of the pacer by myopotentials. |
| UNIP | BIP | Prevents stimulation of the pectoral muscle resulting from contact between the muscle and the pacer housing. Allows a larger amplitude cardiac signal to be picked up because the amplitude is not subject to electrode orientation relative to the depolarization wavefront. |
| UNIP | UNIP | Advantageous for patients with high stimulous thresholds and low cardiac amplitudes. |
| BIP | BIP | Advantageous for patients with high myopotential amplitudes and pectoral muscle stimulation problems. |

Since the operating mode of the input/output circuit may be readily changed by external telemetry apparatus, changes in the patient which might occur following the implant of the pacer, and which would call for a different sensing or pacing lead configuration, can be non-invasively accomplished by the physician.

While the invention has been shown in conjunction with a two-channel A-V type cardiac pacer having atrial and ventricular input/output terminals, it will be appreciated that the input/output circuit of the invention can be used in conjunction with a single channel pacer, as where only a ventricular channel is provided, to provide selective UNIP and BIP pacing and sensing modes in response to an externally applied control signal.

While a particular embodiment of the invention has been shown and described, it will be obvious to those skilled in the art that changes and mofifications may be made without departing from the invention in its broader aspects, and, therefore, the aim in the appended claims is to cover all such changes and modifications as fall within the true spirit and scope of the invention.

We claim:

1. In a cardiac pacer selectively operable in unipolar and bipolar pacing and sensing modes in response to an applied mode designation signal, an input/output circuit comprising:

a source of unidirectional current including a signal ground;

pacer lead terminal means including a cathode electrode and an anode electrode;

a differential sense amplifier operable from said current source, said amplifier having inverting and non-inverting input terminals and providing a sense signal in response to a non-common mode signal applied to said input terminals;

first coupling means for coupling one of said electrodes to one input terminal of said differential amplifier;

second coupling means for coupling the other of said electrodes to the remaining input terminal of said differential amplifier;

means including an output amplifier for generating a pacing pulse, said output amplifier having an output terminal;

third coupling means for coupling said other electrode to said output terminal;

reference terminal means including a reference electrode for establishing electrical contact with a patient's body;

first switching means responsive to a first applied control signal for electively connecting said one electrode to said signal ground;

second switching means responsive to a second applied control signal for selectively connecting said one input terminal of said differential amplifier to said signal ground;

third switching means responsive to a third applied control signal for selectively connecting said reference electrode to said signal ground; and mode control means for generating said first, second and third mode control signals in response to the mode designation signal whereby said first and second switching means are open and said third switching means are closed for unipolar pacing, said first switching means are closed and said second and third switching means are open for bipolar pacing, said first switching means are open and said second and third switching means are closed for unipolar sensing, and said first and second switching means are open for bipolar sensing.

2. A cardiac pacer as defined in claim 1 wherein said switch devices each comprise transistors.

3. A cardiac pacer as defined in claim 1 wherein said coupling means each comprise a capacitor.

4. In a cardiac pacer having atrial and ventricular input/output terminals and selectively operable in unipolar and bipolar pacing and sensing modes in response to an applied command signal, an input/output circuit comprising:

a source of unidirectional current including a signal ground;

atrial pacer lead terminal means including a cathode electrode and an anode electrode;

a differential atrial sense amplifier operable from said unidirectional current source, said amplifier having inverting and non-inverting input terminals and providing an atrial sense signal in response to a non-common mode signal applied to said input terminals;

first atrial coupling means for coupling one of said atrial electrodes to one input terminal of said atrial sense amplifier;

second atrial coupling means for coupling the other of said atrial electrodes to the other input terminal of said atrial sense amplifier;

means including an atrial output amplifier for generating an atrial pacing pulse, said atrial output amplifier having an atrial output terminal;

third atrial coupling means for coupling said other atrial electrode to said atrial output terminal;

ventricular pacing lead terminal means including a cathode electrode and an anode electrode;

a differential ventricular sense amplifier operable from said unidirectional current source, said amplifier having inverting and non-inverting input terminals and providing a ventricular sensd signal in response to a non-common mode signal applied to said input terminals;

first ventricular coupling means for coupling one of said ventricular electrodes to one input terminal of said ventricular sense amplifier;

second ventricular coupling means for coupling the other of said ventricular electrodes to the other input terminal of said ventricular sense amplifier;

means including a ventricular output amplifier for generating a ventricular pacing pulse, said ventricular output amplifier having a ventricular output terminal;

third ventricular coupling means for coupling said other ventricular electrode to said ventricular output terminal;

reference terminal means including a reference electrode for establishing electrical contact with a patient's body;

first atrial and ventricular switching means responsive to a first applied control signal for selectively connecting said one electrode to said signal ground;

second atrial and ventricular switching means responsive to a second applied control signal for selectively connecting said one input terminal of said differential amplifier to said signal ground;

third switching means responsive to a third applied control signal for selectively connecting said reference electrode to said signal ground; and mode control means for generating said first, second and third mode control signals in response to the mode designation signal whereby said first and second switching means are open and said third switching means are closed for unipolar pacing said first switching means are closed and said second and third switching means are open for bipolar pacing, said first switching means are open and said second and third switching means are closed for unipolar sensing, and said first and second switching means are open for bipolar sensing.

5. A cardiac pacer as defined in claim 4 wherein said switch devices each comprise transistors.

6. A cardiac pacer as defined in claims 1 or 4 including telemetering means responsive to an externally applied signal for conditioning said mode control means.

7. A cardiac pacer as defined in claim 4 wherein said coupling means each comprise a capacitor.

* * * * *